(12) United States Patent
Nakajima et al.

(10) Patent No.: US 8,593,633 B2
(45) Date of Patent: Nov. 26, 2013

(54) CURE DEGREE EVALUATION METHOD, CURE DEGREE EVALUATION SHEET, AND CURE DEGREE EVALUATION SYSTEM FOR EVALUATING CURE DEGREE OF ACTIVE ENERGY RAY-CURABLE RESIN COMPOSITION

(75) Inventors: Seiji Nakajima, Kyoto (JP); Tomoyuki Nishida, Kyoto (JP); Naoki Masutani, Kyoto (JP); Tomohiro Fukuhara, Kyoto (JP)

(73) Assignee: OMRON Corporation, Kyoto (JP)

( * ) Notice: Subject to any disclaimer, the term of this patent is extended or adjusted under 35 U.S.C. 154(b) by 37 days.

(21) Appl. No.: 13/202,197

(22) PCT Filed: Jan. 22, 2010

(86) PCT No.: PCT/JP2010/000362
§ 371 (c)(1),
(2), (4) Date: Oct. 12, 2011

(87) PCT Pub. No.: WO2010/098010
PCT Pub. Date: Sep. 2, 2010

(65) Prior Publication Data
US 2012/0026501 A1   Feb. 2, 2012

(30) Foreign Application Priority Data
Feb. 26, 2009   (JP) ................. 2009-044621

(51) Int. Cl.
*G01J 3/46* (2006.01)
*C08C 1/14* (2006.01)
*G01D 18/00* (2006.01)

(52) U.S. Cl.
USPC .................. 356/402; 524/160; 250/252.1

(58) Field of Classification Search
USPC .................. 356/402; 524/160; 250/252.1
See application file for complete search history.

(56) References Cited

U.S. PATENT DOCUMENTS 4,164,492 A * 8/1979 Cooper .................. 523/461
4,965,073 A   10/1990 Maruyama et al.

(Continued)

FOREIGN PATENT DOCUMENTS

JP   2-249296 A   10/1990
JP   9-126887 A   5/1997

(Continued)

OTHER PUBLICATIONS

"New Technology of UV/EB Curing and Application," p. 55, CMC Publishing Co., Ltd., with English translation of relevant sections, 3 pages.

(Continued)

*Primary Examiner* — Kara E. Geisel
*Assistant Examiner* — Sunghee Y Gray
(74) *Attorney, Agent, or Firm* — Osha Liang LLP

(57) ABSTRACT

A cure degree evaluation method for evaluating a cure degree of an active energy ray-curable resin composition is a method for evaluating the cure degree of the active energy ray-curable resin composition includes the steps of: irradiating the active energy ray-curable resin composition with an active energy ray; and evaluating the cure degree of the active energy ray-curable resin composition in accordance with a color of the active energy ray-curable resin composition. The active energy ray-curable resin composition contains at least a radical polymerization compound, a leuco dye, and a radical polymerization initiator.

9 Claims, 4 Drawing Sheets

(56) References Cited

U.S. PATENT DOCUMENTS

| | | |
|---|---|---|
| 6,524,763 B1 | 2/2003 | Kuroda et al. |
| 6,740,466 B1 | 5/2004 | Matsumoto et al. |
| 2007/0191520 A1 | 8/2007 | Sugiki et al. |
| 2010/0276578 A1* | 11/2010 | Shelley et al. ............. 250/252.1 |

FOREIGN PATENT DOCUMENTS

| | | |
|---|---|---|
| JP | 11-140388 A | 5/1999 |
| JP | 2001-209176 A | 8/2001 |
| JP | 2001-242249 A | 9/2001 |
| JP | 2007-225584 A | 9/2007 |
| WO | 2005/100472 A1 | 10/2005 |

OTHER PUBLICATIONS

H. Takase, "Hikari Kokasei Jushi no Kokado to Koka Kyodo no Hyoka," Seikei Kako, 2007, vol. 19, No. 2, pp. 68-74, with partial translation, 22 pages.

International Search Report issued in PCT/JP2010/000362, mailed on Feb. 16, 2010, with translation, 5 pages.

Written Opinion issued in PCT/JP2010/000362, mailed on Feb. 16, 2010, 4 pages.

* cited by examiner

FIG. 8

|  | 0.5s | 2s | 5s | 10s | 30s | 60s | 150s |
|---|---|---|---|---|---|---|---|
| Example 2 |  |  |  |  |  |  |  |
| Example 3 |  |  |  |  |  |  |  |
| Example 4 |  |  |  |  |  |  |  |
| Example 5 |  |  |  |  |  |  |  |
| Example 6 |  |  |  |  |  |  |  |
| Example 7 |  |  |  |  |  |  |  |

CURE DEGREE EVALUATION METHOD, CURE DEGREE EVALUATION SHEET, AND CURE DEGREE EVALUATION SYSTEM FOR EVALUATING CURE DEGREE OF ACTIVE ENERGY RAY-CURABLE RESIN COMPOSITION

TECHNICAL FIELD

The present invention relates to a method for simply and highly accurately evaluating a cure degree of an active energy ray-curable resin composition which is cured by active energy ray irradiation, a cure degree evaluation sheet for use in the method, and a cure degree evaluation system for evaluating the cure degree of the active energy ray-curable resin composition.

BACKGROUND ART

An active energy ray-curable resin composition can be cured by use of an active energy ray such as an ultraviolet ray or an electron beam. The active energy ray-curable resin composition is used in many industrial sectors as a surface coat agent, an adhesive, a pressure sensitive adhesive, a sealing agent, a paint, and the like in view of its transparency, quick-curability, fixability, and the like.

Since the active energy ray-curable resin composition is transparent or semi-transparent, it is difficult to visually determine a cure state of the active energy ray-curable resin composition or presence or absence of a quality abnormality in the active energy ray-curable resin composition. Especially the active energy ray-curable resin composition which is used as an adhesive and insufficiently cured causes many cases of complaints about products. Normally, it is necessary to test a quality of each of the products in terms of a cure degree of the active energy ray-curable resin composition. However, actually, there is no effective and realistic method for testing a product quality.

Therefore, in order to cure the active energy ray-curable resin composition, an excess active energy ray whose amount is not less than a sufficient amount is directed to the active energy ray-curable resin composition, so as to guarantee a cure state of the active energy ray-curable resin composition.

However, even active energy ray irradiation in a sufficient amount cannot determine whether or not a part to which the active energy ray-curable resin composition is applied is irradiated with the active energy ray. Further, it is impossible to detect an unsteady production state such as a deterioration in active energy ray irradiation lamp and/or defocusing of the active energy ray irradiation lamp. Therefore, a method for checking a curing reaction state of the active energy ray-curable resin composition is desired. A method has been known for checking a cure state of a resin composition by a Fourier transform infrared spectroscopy (hereinafter referred to as an FT-IR method) or a method for finding a hardness change (e.g., a Young's modulus) (see the description of "New Technology of UV/EB Curing and Application, p. 55, CMC Publishing CO., LTD.).

The FT-IR method is an analysis method in which an infrared absorbed amount in accordance with a specific functional group is measured by infrared irradiation and a conversion degree of the specific functional group is found by fluctuations in the infrared absorbed amount, so that a cure degree is measured.

In contrast, according to the method for finding a Young's modulus, it is possible to find a cure degree by a change in Young's modulus of a resin composition.

However, such check methods as described above are insufficient in accuracy and require time and cost for carrying out a test. In view of the circumstances, a method is required for more simply checking a curing reaction state of the active energy ray-curable resin composition.

Patent Literature 1 discloses a method for visually checking, by a colored degree of a leuco dye, whether or not an ultraviolet-curable epoxy resin is cured.

Patent Literature 2 discloses a curable pressure sensitive adhesive sheet in which it can be easily visually checked, by a color change, whether or not the curable pressure sensitive adhesive sheet is being cured without fail by light irradiation.

These methods are very simple methods which allow visually checking, by a color change, whether or not a resin is cured.

Patent Literature 3 discloses a method for producing a printed circuit board which is characterized by causing a photosensitive electrodeposition paint to contain a leuco dye. What is disclosed in Patent Literature 3 is as follows: A resist can develop color in a case where a photosensitive resist is formed by use of the photosensitive electrodeposition paint containing the leuco dye. This makes it possible to (i) visually check that the resist has been formed in accordance with a pattern mask and (ii) reduce a rejection rate in a manufacturing process without losing a photosensitivity of an electrodeposition resist.

CITATION LIST

Patent Literature 1
International Publication WO2005/100472 (Publication Date: Oct. 27, 2005)
Patent Literature 2
Japanese Patent Application Publication, Tokukaihei, No. 11-140388 A (Publication Date: May 25, 1999)
Patent Literature 3
Japanese Patent Application Publication, Tokukaihei, No. 2-249296 A (Publication Date: Oct. 5, 1990)

SUMMARY OF INVENTION

Technical Problem

According to such check methods as described in Patent Literatures 1 through 3, a change in color of a resin composition is merely visually checked. Patent Literature 3 discloses that it is possible to check that a resist has been formed in accordance with a pattern mask. However, since whether or not a desired pattern mask is formed has nothing to do with a cure state, Patent Literature 3 raises no problem about evaluating a cure state of a resist.

A visual check as described in Patent Literature 1 or 2 has a problem such that it is possible to check whether or not an active energy ray-curable resin composition is cured but impossible to quantify a curing reactivity (hereinafter also referred to as a cure degree) itself of the active energy ray-curable resin composition. Quantitative evaluation of a cure degree of an active energy ray-curable resin composition is highly important in not only guaranteeing a product quality but also optimizing a product manufacturing process.

The FT-IR method and the method for finding a Young's modulus have a problem such that a cure degree of an active energy ray-curable resin composition can be evaluated quantitatively but with low accuracy and thus these methods have not been put into practice.

The present invention has been made in view of the problems, and an object of the present invention is to provide a method for evaluating a cure degree of an active energy ray-curable resin composition simply, highly accurately, and quantitatively, a cure degree evaluation sheet for use in the method, and a cure degree evaluation system.

Solution to Problem

In view of the problems, inventors of the present invention diligently studied a method for evaluating a cure degree of an active energy ray-curable resin composition simply, highly accurately, and quantitatively. As a result, the inventors found that blending a leuco dye with an active energy ray-curable resin composition makes it possible to check, by a color change, whether or not the active energy ray-curable resin composition is cured. Further, the inventors found that (i) there is a correlation between a color value and a cure degree of a cured product of the active energy ray-curable resin composition. Then, the inventors accomplished the present invention by finding that measurement of a color value of a cured product of an active energy ray-curable resin composition allows evaluating a cure degree of the active energy ray-curable resin composition simply, highly accurately, and quantitatively.

Namely, a cure degree evaluation method in accordance with the present invention for evaluating a cure degree of an active energy ray-curable resin composition is a method for evaluating the cure degree of the active energy ray-curable resin composition, the method including the steps of: irradiating the active energy ray-curable resin composition with an active energy ray; and evaluating the cure degree of the active energy ray-curable resin composition in accordance with a color of the active energy ray-curable resin composition, the active energy ray-curable resin composition containing at least a radical polymerization compound, a leuco dye, and a radical polymerization initiator.

The cure degree evaluation method in accordance with the present invention for evaluating a cure degree of an active energy ray-curable resin composition (hereinafter also simply referred to as a "cure degree evaluation method") uses the active energy ray-curable resin composition containing at least a radical polymerization compound, a leuco dye, and a radical polymerization initiator. Therefore, a radical generated from the radical polymerization initiator by active energy ray irradiation causes a polymerization reaction (e.g., a main chain reaction and a cross-linking reaction) of a radical polymerization compound, so that the active energy ray-curable resin composition is cured.

The active energy ray-curable resin composition containing the leuco dye is colorless before being subjected to active energy ray irradiation. When the active energy ray-curable resin composition is irradiated with an active energy ray and receives the radical from the radical polymerization initiator, an ionization reaction occurs in the leuco dye contained in the active energy ray-curable resin composition, so that the leuco dye is colored in blue. Since such a coloring reaction is irreversible, it is possible to record active energy ray irradiation history.

There is a correlation between an amount of the generated radical and the cure degree of the active energy ray-curable resin composition. Further, the amount of the generated radical and a colored degree of the leuco dye correlate to each other. Namely, a degree of polymerization of the radical polymerization compound contained in the active energy ray-curable resin composition can be directly checked through the colored degree of the leuco dye.

FIG. 1 illustrates a change in colored degree of an active energy ray-curable resin composition with respect to a length (second) of ultraviolet irradiation time in a case where an ultraviolet ray is directed as an active energy ray to the active energy ray-curable resin composition. A colored degree of an active energy ray-curable resin composition containing a leuco dye changes in accordance with a length of ultraviolet irradiation time (see FIG. 1). Note that each of 0.5 s to 150 s shown in FIG. 1 indicates ultraviolet irradiation time (second(s)). Note also that a length of ultraviolet irradiation time and a cure degree of an active energy ray-curable resin composition correlate to each other. This makes it possible to evaluate a cure degree of an active energy ray-curable resin composition from a colored degree of the active energy ray-curable resin composition.

According to the cure degree evaluation method in accordance with the present invention, it is possible to simply evaluate a product cure quality. It is also possible to detect, on a real-time basis, a production change which is normally difficult to check such as a deterioration of a lamp emitting an active energy ray and/or a change in irradiation position. Further, the cure degree evaluation method in accordance with the present invention facilitates optimization of a production process such as consideration of a highly efficient active energy ray irradiation method.

A conventional check method has a problem of having low evaluation accuracy. In contrast, according to the cure degree evaluation method in accordance with the present invention for evaluating a cure degree of an active energy ray-curable resin composition, an evaluation result is highly reliable since a cure degree is evaluated highly accurately (see Examples described later).

According to the curable pressure sensitive adhesive sheet described in Patent Literature 2, a cure degree of the sheet is indicated by a transmittance of the sheet. For example, since a transmittance decreases in a cloudy active energy ray-curable resin composition or an active energy ray-curable resin composition with which a filler is mixed, an evaluation accuracy dramatically deteriorates. In contrast, according to the cure degree evaluation method in accordance with the present invention, a cure degree is evaluated from a color (e.g., a color value using reflected light) of an active energy ray-curable resin composition, there is no fear that an evaluation accuracy may deteriorate even in a cloudy active energy ray-curable resin composition or an active energy ray-curable resin composition with which a filler is mixed. Accordingly, the cure degree evaluation method in accordance with the present invention is different from the method described in Patent Literature 2 for carrying out a cure degree evaluation by use of a transmittance in that a cure degree is evaluated from a color value in the cure degree evaluation method in accordance with the present invention. The cure degree evaluation method in accordance with the present invention also yields a highly remarkable effect.

A cure degree evaluation system in accordance with the present invention (hereinafter also simply referred to as a "cure degree evaluation system") is a cure degree evaluation system for evaluating a cure degree of an active energy ray-curable resin composition containing at least a radical polymerization compound, a leuco dye, and a radical polymerization initiator, the cure degree evaluation system including: irradiation means for irradiating the active energy ray-curable resin composition with an active energy ray; and cure state check means for evaluating the cure degree of the active energy ray-curable resin composition by measuring a color of a part in which the cure degree of the active energy ray-curable resin composition is evaluated.

According to the cure degree evaluation system in accordance with the present invention, it is possible to automatically evaluate a cure degree of an active energy ray-curable resin composition while curing the active energy ray-curable resin composition. Accordingly, it is possible to reduce insufficiently cured products.

A cure degree check sheet in accordance with the present invention (hereinafter also simply referred as a "cure degree check sheet") is a cure degree check sheet for evaluating a cure degree of an active energy ray-curable resin composition, the cure degree check sheet including a sheet-formed transparent resin material to which a chemical solution containing at least a radical polymerization compound, a leuco dye, and a radical polymerization initiator is applied.

The cure degree check sheet in accordance with the present invention includes a sheet-formed transparent resin material to which a chemical solution containing at least a radical polymerization compound, a leuco dye, and a radical polymerization initiator is applied. According to the arrangement, the cure degree check sheet is colored in accordance with an amount of radicals generated by active energy ray irradiation. Therefore, the cure degree check sheet can serve as means for indirectly but simply and promptly evaluating a cure degree of an active energy ray-curable resin composition subjected to active energy ray irradiation while checking a colored degree of the cure degree check sheet.

A cure degree evaluation method in accordance with the present invention for evaluating a cure degree of an active energy ray-curable resin composition is a method for evaluating the cure degree of the active energy ray-curable resin composition, the method including the steps of: carrying out active energy ray irradiation simultaneously with respect to the cure degree check sheet recited in claim 9 and a part to which the active energy ray-curable resin composition is applied; and evaluating the cure degree of the active energy ray-curable resin composition in accordance with a color of the cure degree check sheet.

According to the arrangement, it is possible to indirectly but simply and promptly evaluate a cure degree of an active energy ray-curable resin composition subjected to active energy ray irradiation while checking a colored degree of the cure degree check sheet. Accordingly, a shape of a part to which an active energy ray-curable resin composition is applied is less likely to restrict an evaluation of a cure degree of the active energy ray-curable resin composition.

In a case where an active energy ray-curable resin composition is cured in the presence of oxygen, a generated radical is captured by oxygen. Therefore, curing of a resin composition does not progress only in a top layer of the active energy ray-curable resin composition which layer is exposed to air, and a surface tack may occur due to an uncured resin composition. In a case where a resin composition whose top surface is provided with the cure degree check sheet is cured in an embodiment of the present invention, the resin composition has no part in which the resin composition and oxygen are in contact with each other. According to this, it is possible to reduce inhibition of curing of a resin composition due to oxygen and a surface tack due to an uncured resin surface.

Advantageous Effects of Invention

A cure degree evaluation method in accordance with the present invention for evaluating a cure degree of an active energy ray-curable resin composition includes the steps of: irradiating the active energy ray-curable resin composition with an active energy ray; and evaluating the cure degree of the active energy ray-curable resin composition in accordance with a color of the active energy ray-curable resin composition, the active energy ray-curable resin composition containing at least a radical polymerization compound, a leuco dye, and a radical polymerization initiator. Therefore, the cure degree evaluation method yields an effect of evaluating a cure degree of an active energy ray-curable resin composition simply, highly accurately, and quantitatively.

A cure degree evaluation system in accordance with the present invention (hereinafter also simply referred to as a "cure degree evaluation system") includes: irradiation means for irradiating the active energy ray-curable resin composition with an active energy ray; and cure state check means for evaluating the cure degree of the active energy ray-curable resin composition by measuring a color of a part in which the cure degree of the active energy ray-curable resin composition is evaluated. According to the cure degree evaluation system in accordance with the present invention, it is possible to automatically evaluate a cure degree of an active energy ray-curable resin composition while curing the active energy ray-curable resin composition. Accordingly, the cure degree evaluation system in accordance with the present invention yields an effect of reducing insufficiently cured products.

A cure degree check sheet in accordance with the present invention is a cure degree check sheet for evaluating a cure degree of an active energy ray-curable resin composition, the cure degree check sheet including a sheet-formed transparent resin material to which a chemical solution containing at least a radical polymerization compound, a leuco dye, and a radical polymerization initiator is applied. Therefore, the cure degree check sheet yields an effect of serving as means for indirectly but simply and promptly evaluating a cure degree of an active energy ray-curable resin composition subjected to active energy ray irradiation while checking a colored degree of the cure degree check sheet.

BRIEF DESCRIPTION OF DRAWINGS

FIG. 8 illustrates colored degrees of active energy ray-curable resin compositions obtained in Examples 2 through 7 for each ultraviolet irradiation time.

DESCRIPTION OF EMBODIMENTS

Figure 1:
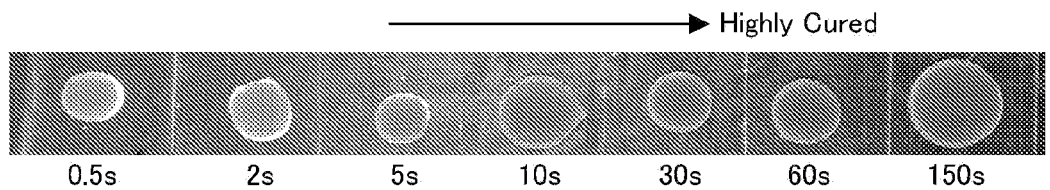
FIG. 1 illustrates a change in colored degree of an active energy ray-curable resin composition in accordance with the present invention with respect to a length (second) of ultraviolet irradiation time.

An embodiment of the present invention is described below. However, the present invention is not limited to this.

Note that "A to B" herein indicating a range refers to not less than A and not more than B".

[1. Cure Degree Evaluation Method for Evaluating Cure Degree of Active Energy Ray-Curable Resin Composition]

An object of a cure degree evaluation method in accordance with the present invention for evaluating a cure degree of an active energy ray-curable resin composition is to evaluate the cure degree of the active energy ray-curable resin composition. Such an active energy ray-curable resin composition is mainly a liquid before being subjected to active energy ray irradiation, whereas the active energy ray-curable resin composition is cured to be a solid after being subjected to active energy ray irradiation. An "active energy ray-curable resin composition" is herein used in a generic meaning irrespective of its state (its liquid state before active energy ray irradiation or its solid state after active energy ray irradiation). Note that an active energy ray-curable resin composition to be evaluated by the cure degree evaluation method in accordance with the present invention can be used as a surface coat agent, an adhesive, a pressure sensitive adhesive, a sealing agent, a paint, and the like. However, what is to be evaluated by the present invention is not limited to these.

An active energy ray for use in curing the active energy ray-curable resin composition is exemplified by an ultraviolet ray and an electron beam. However, the present invention is not limited to these. In particular, it is more preferable to use an ultraviolet ray as the active energy ray since the ultraviolet ray can be used at normal pressure.

According to an embodiment of the present invention, a cure degree evaluation method in accordance with the present invention for evaluating a cure degree of an active energy ray-curable resin composition (hereinafter may be simply referred to as a "cure degree evaluation method") includes the steps of: irradiating the active energy ray-curable resin composition with an active energy ray; and evaluating the cure degree of the active energy ray-curable resin composition in accordance with a color of the active energy ray-curable resin composition, the active energy ray-curable resin composition containing at least a radical polymerization compound, a leuco dye, and a radical polymerization initiator.

According to another embodiment of the present invention, the cure degree evaluation method in accordance with the present invention for evaluating a cure degree of an active energy ray-curable resin composition includes the steps of: carrying out active energy ray irradiation simultaneously with respect to a cure degree check sheet in accordance with the present invention and a part to which the active energy ray-curable resin composition is applied; and evaluating the cure degree of the active energy ray-curable resin composition in accordance with a color of the cure degree check sheet.

Therefore, the following description specifically discusses the "active energy ray-curable resin composition", the "cure degree check sheet", and the "cure degree evaluation method for evaluating a cure degree of an active energy ray-curable resin composition".

(1-1. Active Energy Ray-Curable Resin Composition)

An active energy ray-curable resin composition used in the cure degree evaluation method in accordance with the present invention for evaluating a cure degree of an active energy ray-curable resin composition contains at least radical polymerization compound, a leuco dye, and a radical polymerization initiator.

Note that the "radical polymerization compound" refers a chemical compound which reacts with a radical generated from a radical polymerization initiator by active energy ray irradiation, so as to be addition polymerized. The "radical polymerization compound" may be a monomer, an oligomer, or a polymer. Note that the monomer is also referred to as a monomeric substance and refers to a material from which a polymer (polymeric substance) is synthesized by a polymerization reaction. In contrast, the oligomer is also referred to as a low polymer having comparative low polymerization degree of 2 to 20 or so.

It is preferable that the radical polymerization compound, which is not particularly limited, be selected from the group consisting of acrylate, methacrylate, vinyl ether, and allyl ether.

Examples of the "acrylate" include tetrahydrofurfuryl acrylate, stearyl acrylate, isobornyl acrylate, 2-hydroxyethyl acrylate, dimethylaminoethyl acrylate, 2-hydroxy-3-phenoxypropyl methacrylate, ωcarboxy-polycaprolactone monoacrylate, phthalic acid monohydroxyethyl acrylate, hexahydrophthalic acid monohydroxyethyl acrylate, bisphenol AEO denatured diacrylate, tricyclodecanedimethylol diacrylate, polyethylene glycol diacrylate, polypropylene glycol diacrylate, pentaerythritol trimethacrylate, pentaerythritol tetramethacrylate, and dimethylol propane tetraacrylate.

Examples of the "methacrylate" include tetrahydrofurfuryl methacrylate, stearyl methacrylate, isobornyl methacrylate, 2-hydroxyethyl methacrylate, dimethylaminoethyl methacrylate, 2-hydroxy-3-phenoxypropyl methacrylate, ωcarboxy-polycaprolactone monomethacrylate, phthalic acid monohydroxyethyl methacrylate, hexahydrophthalic acid monohydroxyethyl methacrylate, bisphenol AEO denatured dimethacrylate, tricyclodecanedimethylol dimethacrylate, polyethylene glycol dimethacrylate, polypropylene glycol dimethacrylate, pentaerythritol trimethacrylate, pentaerythritol tetramethacrylate, and dimethylol propane tetramethacrylate.

Examples of the "vinyl ether" include ethylene glycol divinyl ether, butanediol divinyl ether, cyclohexanedimethanol divinyl ether, cyclohexandiol divinyl ether, trimethylolpropane trivinyl ether, hydroxyethyl vinyl ether, hydroxybutyl vinyl ether, cyclohexanedimethanol monovinyl ether, cyclohexandiol monovinyl ether, 9-hydroxynonylvinyl ether, and propylene glycol monovinyl ether.

Examples of the "acrylic ether" include trimethylolpropane diaryl ether, pentaerythritol triaryl ether, glycerin monoallyl ether, allyl glycidyl ether, and triallyl isocyanurate.

The radical polymerization compounds mentioned above may be used alone or in combination of two or more kinds.

The radical polymerization compound is contained in an amount preferably of 10% by weight to 99.5% by weight, and more preferably of 20% by weight to 99.5% by weight, with respect to the active energy ray-curable resin composition. In a case where the radical polymerization compound is contained in an amount of not less than 10% by weight with respect to the active energy ray-curable resin composition, the active energy ray-curable resin composition can be cured sufficiently.

The "leuco dye", which is normally colorless or light-colored, is not particularly limited provided that the leuco dye is a substance which is colored by reacting with a radical generated from a radical polymerization initiator by active energy ray irradiation. In what color the leuco dye is colored is not particularly limited, either. It is preferable that the leuco dye be selected from the group consisting of leuco crystal violet, leuco malachite green, leuco crystal violet lactone, leuco quinizarine, benzoyl leucomethylene blue, 2'-(2-chloroanilino)-6'-(dibutylamino)fluorane, and 3',6-bis(dimethylamino)-2-(4-nitrophenyl)spiro[isoindole-1,9'-xanthene]-3-on.

The leuco dyes mentioned above may be used alone or in combination of two or more kinds.

The leuco dye is contained in an amount preferably of 0.001% by weight to 10% by weight, and more preferably of 0.01% by weight to 3% by weight, with respect to the active energy ray-curable resin composition. In a case where the leuco dye is contained in an amount of not less than 0.001% by weight with respect to the active energy ray-curable resin composition, a colored degree of the active energy ray-curable resin composition can be easily checked. Further, since a color change can be easily checked, it is preferable that the leuco dye be contained in an amount of not more than 10% by weight with respect to the active energy ray-curable resin composition.

Examples of the "radical polymerization initiator" include a photopolymerization initiator and a thermal polymerization initiator. The present invention employs a photopolymerization initiator for use in a photopolymerization (photo-curing) reaction.

Examples of the "photopolymerization initiator", which is not particularly limited, include 2,4,6-trymethylbenzoyl-diphenyl-phosphine oxide (e.g., product name: Lucirin TPO, produced by BASF A.G.), 2-hydroxy-2-methyl-1-phenyl-propene-1-on, 2-methyl-1-[4-(methylthio)phenyl]-2-morpholinopropene-1-on, 2,4,6-trymethylbenzoyl-diphenyl-phosphine oxide, triphenylsulfonyltriflate, 1-hydroxy-cyclohexylphenylketone, 2,2-dimethoxy-1,2-diphenylethane-1-on, and 2-methyl-1[4-(methylthio)phenyl]-2-morpholinopropane-1-on.

The radical polymerization initiators mentioned above may be used alone or in combination of two or more kinds.

The radical polymerization initiator is contained in an amount preferably of 0.01% by weight to 10% by weight, and more preferably of 0.1% by weight to 5% by weight, with respect to the active energy ray-curable resin composition. In a case where the radical polymerization initiator is contained in an amount of not less than 0.01% by weight with respect to the active energy ray-curable resin composition, a radical polymerization reaction can be caused sufficiently. Further, since it is possible to prevent a reduction in amount of radical generation due to a reduction in transmittance of an active energy ray, it is preferable that the radical polymerization initiator be contained in an amount of not more than 10% by weight with respect to the active energy ray-curable resin composition.

It is preferable that the active energy ray-curable resin composition further contain an inorganic filler in addition to the radical polymerization compound, the leuco dye, and the radical polymerization initiator. The active energy ray-curable resin composition which further contains the inorganic filler is cloudy. Therefore, use of such an active energy ray-curable resin composition makes it easy to check a color change. Furthermore, use of such an active energy ray-curable resin composition yields an effect of enhancing rigidity of the active energy ray-curable resin composition. Moreover, use of such an active energy ray-curable resin composition yields an effect of reducing a shrinkage of a cured resin.

Examples of the "inorganic filler", which is not particularly limited, include silica and glass bead.

The inorganic fillers mentioned above may be used alone or in combination of two or more kinds.

The inorganic filler is contained in an amount preferably of 5% by weight to 90% by weight, and more preferably of 30% by weight to 85% by weight, with respect to the active energy ray-curable resin composition. In a case where the inorganic filler is contained in an amount of not less than 5% by weight with respect to the active energy ray-curable resin composition, the resulting active energy ray-curable resin composition is cloudy and a colored degree of the leuco dye can be easily checked. Furthermore, rigidity of the active energy ray-curable resin composition is enhanced. Moreover, a shrinkage of a cured resin is reduced. Since a color change can be easily checked, it is preferable that the inorganic filler be contained in an amount of not more than 90% by weight with respect to the active energy ray-curable resin composition.

The active energy ray-curable resin composition may contain an organic solvent, a silane coupling agent, and the like in addition to the radical polymerization compound, the leuco dye, the radical polymerization initiator, and the inorganic filler.

(1-2. Cure Degree Check Sheet)

A cure degree check sheet in accordance with the present invention is used to evaluate a cure degree of an active energy ray-curable resin composition cured by active energy ray irradiation. The cure degree check sheet is obtained by applying, to a sheet-formed transparent resin material, a chemical solution containing at least a radical polymerization compound, a leuco dye, and a radical polymerization initiator.

The "radical polymerization compound", the "leuco dye", and the "radical polymerization initiator" are as described earlier in "1-1. Active Energy Ray-curable Resin Composition".

The chemical solution used for preparing the cure degree check sheet may contain an organic solvent, a polymer, an inorganic filler, a silane coupling agent, and the like in addition to the radical polymerization compound, the leuco dye, and the radical polymerization initiator which are described above. Assume that the cure degree check sheet is used in its semi-cured state. In a case where the chemical solution used for preparing the cure degree check sheet contains the polymer and the organic solvent, the cure degree check sheet can be semi-cured easily.

The "sheet" refers to a thin film and is synonymous with a "film". The "transparent resin material" is not particularly limited provided that the "transparent resin material" is made of a transparent resin. Examples of the "transparent resin material" include PET, PP, polyester, and nylon. The "sheet-formed transparent resin material" refers to a material obtained by causing the transparent resin to be thin film-formed.

The "sheet-formed transparent resin material" is not particularly limited provided that the "sheet-formed transparent resin material" can transmit an active energy ray. Examples of the "sheet-formed transparent resin material" include a PET sheet, a PP sheet, a polyester sheet, and a nylon sheet. What is commercially available can be used as the PET sheet, the PP sheet, the polyester sheet, the nylon sheet, or the like. Further, a thickness of the transparent resin material is not particularly limited. For example, it is possible to use a transparent resin material having a thickness of 10 μm to 5 μm. Note that a thickness of the transparent resin material is preferably as uniform as possible.

How to apply the chemical solution to the sheet is not particularly limited provided that the chemical solution can be applied to the sheet in a uniform thickness. For example, the chemical solution can be applied to the sheet in a uniform thickness by use of conventionally publicly known screen printing, gravure printing, sprayed coat dipping, or the like.

The chemical solution to be applied to the sheet has a thickness preferably of 1 µm to 300 µm, and more preferably of 10 µm to 150 µm. In a case where the chemical solution to be applied to the sheet has a thickness in such a range, it is possible to check a change in color of the cure degree check sheet without inhibiting curing of the active energy ray-curable resin composition.

The cure degree check sheet may also be obtained by semi-curing the chemical solution which has been applied to the sheet. Note that a "semi-cured" state herein refers to a state in which the active energy ray-curable resin composition reacts to further active energy ray irradiation and leaves room to be cured but has little fluidity.

The "semi-curing" is carried out by, for example, a method for heating a sheet to which a chemical solution has been applied. The sheet is heated at a temperature preferably of 40° C. to 150° C., and more preferably of 40° C. to 80° C. The "semi-curing" may also be carried out by active energy ray irradiation in an ultralow amount. For example, in a case where an ultraviolet ray is used as an active energy ray in active energy ray irradiation, it is preferable that the ultraviolet ray have an illuminance of 0.5 mW to 20 mW and irradiation time be 0.1 s to 20 s. An active energy ray other than the ultraviolet ray may also be employed by appropriately considering an irradiation condition which is suitable for semi-curing.

(1-3. Cure Degree Evaluation Method)

A cure degree evaluation method in accordance with the present invention uses the active energy ray-curable resin composition or the cure degree check sheet in accordance with the present invention (described earlier) to evaluate a cure degree of an active energy ray-curable resin composition. The following description discusses a cure degree evaluation method using an active energy ray-curable resin composition and a cure degree evaluation method using a cure degree check sheet.

(i) Cure Degree Evaluation Method Using Active Energy Ray-Curable Resin Composition A cure degree evaluation method using an active energy ray-curable resin composition uses the active energy ray-curable resin composition described earlier in "1-1. Active Energy Ray-curable Resin Composition" to evaluate a cure degree in accordance with a color of the active energy ray-curable resin composition. The active energy ray-curable resin composition in accordance with the present invention is colored by, for example, ultraviolet irradiation. Therefore, in a case where a colored degree of the active energy ray-curable resin composition is checked, it is possible to evaluate a cure degree of the active energy ray-curable resin composition simply and promptly.

An embodiment of the present invention is preferably arranged such that a cure degree of the active energy ray-curable resin composition is evaluated by comparing a color of the active energy ray-curable resin composition and a reference color. Note here that the "reference color" refers to a color sample preliminarily prepared for various cure degrees. Since there is a correlation between ultraviolet irradiation time, i.e., a cure degree of an active energy ray-curable resin composition and a color of the active energy ray-curable resin composition (see FIG. 1), it is possible to simply evaluate a cure degree of a resin composition by visually comparing the color sample and the color of the active energy ray-curable resin composition.

Note that a correlation between a cure degree and a color of an active energy ray-curable resin composition may vary depending on a composition, a curing condition, and/or the like of the active energy ray-curable resin composition. Therefore, it is possible to evaluate a cure degree more accurately by preparing a color sample for an active energy ray-curable resin composition whose cure degree is required to be evaluated and comparing a color of the active energy ray-curable resin composition and the color sample.

Another embodiment of the present invention is preferably arranged such that a cure degree of the active energy ray-curable resin composition is evaluated by measuring a color value of the active energy ray-curable resin composition. Note here that a color system whose color value is to be measured is not particularly limited. Examples of the color system include a La*b* color system, a Lu*v* color system, an xyY color system, and an RGB color system.

Color values of these color systems can be measured by use of cure state check means such as a color difference meter.

In a case where a calibration curve showing a relationship between a cure degree and a color value is prepared, it is possible to quantitatively calculate a cure degree from a color value in accordance with the calibration curve. Such a method makes it possible to evaluate a cure degree more accurately and quantitatively than a visual color check.

For example, assume that each of X, Y, and Z color values obtained 0.5 second after active energy ray irradiation is a cure degree of 0% and each of X, Y, and Z color values obtained 150 seconds after active energy ray irradiation is a cure degree of 100%. In a case where the X color value is $X_t$ t seconds after active energy ray irradiation, an evaluation formula for a cure degree of an active energy ray-curable resin composition subjected to active energy ray irradiation for t seconds can be represented by the following equation (1). Y and Z cure degrees can be similarly found.

$$\text{Cure degree (\%)} = |(X_t - X_{0.5})/(X_{150} - X_{0.5})| \times 100 \quad (1)$$

Still another embodiment of the present invention is preferably arranged such that a part in which the cure degree of the active energy ray-curable resin composition is evaluated is provided separately from a part to which the active energy ray-curable resin composition is to be applied.

Note here that the "part in which the cure degree of the active energy ray-curable resin composition is evaluated" refers to a part in which the cure degree of the active energy ray-curable resin composition is evaluated in accordance with a color. Note also that the "part to which the active energy ray-curable resin composition is to be applied" refers to a part to which the active energy ray-curable resin composition is applied to attain an object. For example, in a case where the active energy ray-curable resin composition is used as an adhesive, the "part to which the active energy ray-curable resin composition is to be applied" refers to a part to which the active energy ray-curable resin composition is applied to cause members to adhere to each other. Alternatively, in a case where the active energy ray-curable resin composition is used as a sealing agent, the "part to which the active energy ray-curable resin composition is to be applied" refers to a part to which the active energy ray-curable resin composition is applied to partially seal a member.

Note that, for example, in the case where the active energy ray-curable resin composition is used as an adhesive, the "object" is to cause members to adhere to each other. However, according to the cure degree evaluation method of the present invention, it does not matter whether or not the "object" has been attained in the "part to which the active energy ray-curable resin composition is to be applied". Namely, since an object of the present invention is to evaluate a cure degree, for example, in the case where the active energy ray-curable resin composition is used as an adhesive, it does not matter whether or not a desired adhering effect is actually obtained.

Note also that "a part in which the cure degree of the active energy ray-curable resin composition is evaluated is provided separately from a part to which the active energy ray-curable resin composition is to be applied" refers to a state in which the active energy ray-curable resin composition is applied to a part that is different from the part in which such an object as described above is attained.

An example is described below with reference to FIG. 7. (a) of FIG. 7, which shows an embodiment of the present invention, schematically illustrates that in order to evaluate a cure degree of the active energy ray-curable resin composition, a lead-in section is provided in a member separately from a part to which the active energy ray-curable resin composition is to be applied. A lead-in section 21 is provided as the "part in which the cure degree of the active energy ray-curable resin composition is evaluated" separately from a part 22 to which the active energy ray-curable resin composition is to be applied. Even in a case where the part to which the active energy ray-curable resin composition is to be applied is indefinite in shape and it is difficult to evaluate the cure degree accurately, it is possible to easily evaluate the cure degree of the active energy ray-curable resin composition by providing the lead-in section 21 in a part which is easy to test.

Figure 7:
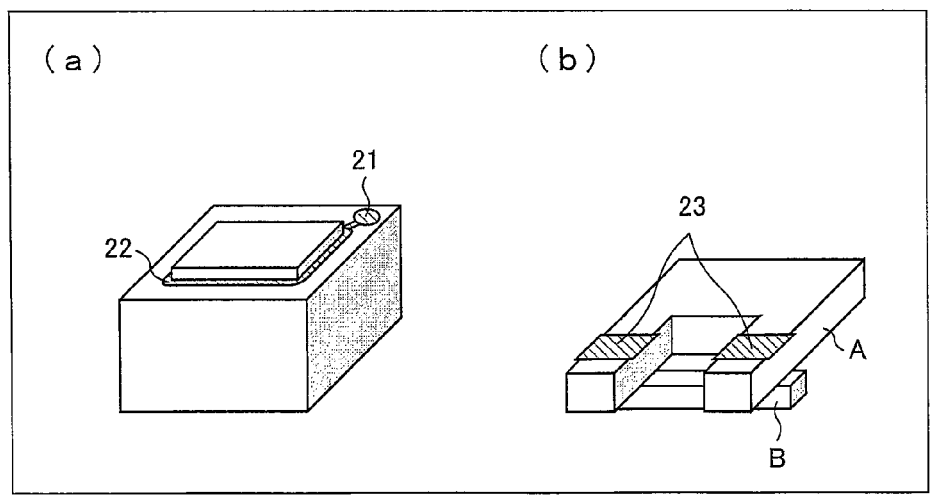
FIG. 7 shows the embodiment of the present invention. (a) of FIG. 7 schematically illustrates that in order to evaluate a cure degree of the active energy ray-curable resin composition, a lead-in section is provided in a member separately from a part to which the active energy ray-curable resin composition is to be applied. (b) of FIG. 7 schematically illustrates that in order to evaluate a cure degree of an active energy ray-curable resin, a part of a member is provided with an observation window so that a colored degree of an inner part of the member to which part the active energy ray-curable resin composition is to be applied can be checked.

(b) of FIG. 7, which shows another embodiment of the present invention, schematically illustrates that in order to evaluate a cure degree of an active energy ray-curable resin, a part of a member is provided with an observation window so that a colored degree of an inner part of the member to which part the active energy ray-curable resin composition is to be applied can be checked. In (b) of FIG. 7, the "part of the member to which part the active energy ray-curable resin composition is to be applied" refers to a part in which a member A and a member B adhere to each other. It is difficult to directly evaluate a color of the part to which the active energy ray-curable resin composition is to be applied (see (b) of FIG. 7). Therefore, since preparation of observation windows 23 for the member A allows checking a colored degree of an inner part of the member A to which part the active energy ray-curable resin composition is to be applied, it is possible to easily evaluate the cure degree of the active energy ray-curable resin composition.

Note that an active energy ray-curable resin composition in accordance with the present invention can be cured by active energy ray irradiation. Note also that the active energy ray-curable resin composition is colored by active energy ray irradiation. Therefore, for example, in a case where the active energy ray-curable resin composition in accordance with the present invention is used as an adhesive, at least one of members which adhere to each other with the adhesive is preferably a material which can transmit an active energy ray (hereinafter referred to as a "transmissive material") such as quartz or an organic material. According to this, it is possible to cause the transmissive material to irradiate the active energy ray-curable resin composition with an active energy ray and to easily check a colored degree of the active energy ray-curable resin composition. For example, in a case where a transparent transmissive material (not illustrated) is used as one of adhering members, it is possible to directly check, from the transparent material side, a colored degree of the active energy ray-curable resin composition.

Examples of the transmissive material include quartz, alkali glass, borosilicate glass, acrylic, polycarbonate, polyolefin, and transparent polyimide. However, the transmissive material is not limited to these.

(ii) Cure Degree Evaluation Method Using Cure Degree Check Sheet

A cure degree evaluation method using a cure degree check sheet includes the steps of: carrying out active energy ray irradiation simultaneously with respect to a cure degree check sheet described earlier in "1-2. Cure Degree Check sheet" and a part to which an active energy ray-curable resin composition is applied; and evaluating a cure degree of the active energy ray-curable resin composition in accordance with a color of the cure degree check sheet.

The cure degree check sheet in accordance with the present invention is colored by active energy ray irradiation. Accordingly, in a case where a colored degree of the cure degree check sheet is checked, a cure degree of an active energy ray-curable resin composition which has been irradiated with an active energy ray and contains no leuco dye can be simultaneously evaluated indirectly but simply and promptly.

It is not particularly limited in the step of "carrying out active energy ray irradiation" where the cure degree check sheet is provided, provided that active energy ray irradiation can be carried out simultaneously with respect to the cure degree check sheet and the part which is to be evaluated and to which the active energy ray-curable resin composition is applied. For example, the cure degree check sheet can be provided on or under the part which is to be evaluated and to which the active energy ray-curable resin composition is applied. Since the cure degree check sheet colored by active energy ray irradiation can transmit an active energy ray, it seems that the active energy ray-curable resin composition is less likely to be inhibited from being cured even in a case where the cure degree check sheet is provided on the part to which the active energy ray-curable resin composition is applied (see Examples described later).

In particular, in a case where a resin composition is cured in a state in which the cure degree check sheet is provided on a part to which the resin composition is applied, the resin composition has no part in which the resin composition is in contact with oxygen. According to this, it is possible to reduce (i) inhibition by oxygen of curing of the resin composition and (ii) a surface tack due to an uncured resin surface. Therefore, it is preferable that the resin composition be cured in such a state.

In a case where the cure degree check sheet and the active energy ray-curable resin composition whose cure degree is to be evaluated and which contains no leuco dye are different in composition and are irradiated with an active energy ray under an identical condition, the cure degree check sheet and the active energy ray-curable resin composition seem to be different in curing reaction state and it is difficult to evaluate the cure degree accurately. Therefore, it is preferable that the cure degree check sheet for use in such a cure degree evaluation method be identical in composition to the active energy ray-curable resin composition whose cure degree is to be evaluated and which contains no leuco dye, except that the cure degree check sheet contains a leuco dye, an organic solvent, and a polymer.

An embodiment of the present invention is preferably arranged such that a cure degree of the active energy ray-curable resin composition is evaluated by comparing a color of the active energy ray-curable resin composition and a reference color. How to compare a color of the active energy ray-curable resin composition and a reference color and how to evaluate a cure degree of the active energy ray-curable resin composition are as described earlier in "(i) Cure Degree Evaluation Method Using Active Energy Ray-curable Resin Composition" of "1-3. Cure Degree Evaluation Method".

Another embodiment of the present invention is preferably arranged such that a cure degree of the active energy ray-curable resin composition is evaluated by measuring a color value of the cure degree check sheet. What kind of color value to be measured, how to measure the color value, and how to evaluate the cure degree are as described earlier in "(i) Cure Degree Evaluation Method Using Active Energy Ray-curable Resin Composition" of "1-3. Cure Degree Evaluation Method".

[2. Cure Degree Evaluation System]

A cure degree evaluation system in accordance with the present invention is capable of automatically evaluating a cure degree of an active energy ray-curable resin composition while irradiating the active energy ray-curable resin composition with an active energy ray so as to cure the active energy ray-curable resin composition, the active energy ray-curable resin composition containing at least a radical polymerization compound, a leuco dye, and a polymerization initiator.

Accordingly, the cure degree evaluation system in accordance with the present invention includes: irradiation means for irradiating the active energy ray-curable resin composition with an active energy ray; and cure state check means for evaluating the cure degree of the active energy ray-curable resin composition by measuring a color of a part in which the cure degree of the active energy ray-curable resin composition is evaluated.

The "irradiation means" is not particularly limited provided that the "irradiation means" is capable of irradiating the active energy ray-curable resin composition with an active energy ray. The "active energy ray", which is not particularly limited, is exemplified by an ultraviolet ray and an electron beam. In particular, it is more preferable to use an ultraviolet ray since the ultraviolet ray can be used at normal pressure.

The "cure state check means" is not particularly limited provided that the "cure state check means" is capable of evaluating the cure degree of the active energy ray-curable resin composition by measuring a color of a part in which the cure degree of the active energy ray-curable resin composition is evaluated. How to measure the "color" is exemplified by a method in which a color value of the active energy ray-curable resin composition can be measured by use of a color difference meter. Note that the "cure state check means" may include evaluation means for evaluating the cure degree of the active energy ray-curable resin composition in accordance with the color thus measured.

In addition to the "irradiation means" and the "cure state check means" which are described earlier, the cure degree evaluation system in accordance with the present invention may further include: a position control apparatus for carrying out position control so that light from the cure state check means is directed to the part in which the cure degree of the active energy ray-curable resin composition is evaluated; a display device and/or a sorting apparatus for determining whether or not the active energy ray-curable resin composition whose cure degree has been evaluated is acceptable and classifying the active energy ray-curable resin composition as an acceptable product or an unacceptable product.

Figure 6:
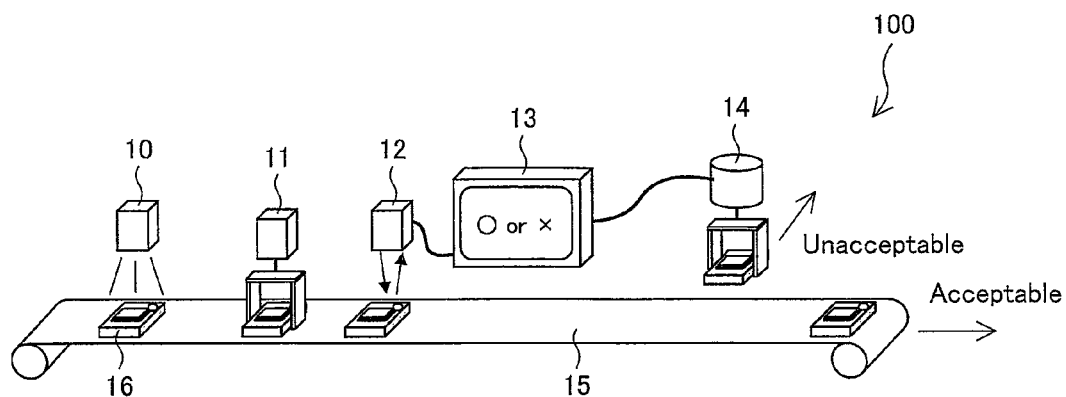
FIG. 6, which shows an embodiment of the present invention, schematically illustrates a cure degree evaluation system.

The following description discusses an embodiment of the cure degree evaluation system with reference to FIG. 6. FIG. 6 schematically illustrates an example of a cure degree evaluation system 100 in accordance with the present invention. The cure degree evaluation system 100 includes a light source (irradiation means) 10, a position control apparatus (position control means) 11, a color difference meter (cure state check means) 12, testing software (evaluation means) 13, a sorting apparatus (sorting means) 14, and a stage 15. An evaluation sample 16 that is to be tested is provided on the stage 15.

The cure degree evaluation system in accordance with the present invention includes the light source (irradiation means) 10 which irradiates the active energy ray-curable resin composition with an active energy ray. In a case where an ultraviolet ray is used as the active energy ray in an embodiment of the present invention, examples of the "light source" include an ultra-high pressure mercury lamp, a high-pressure mercury lamp, a low-pressure mercury lamp, a metal halide lamp, an LED lamp, a carbon arc lamp, and a xenon lamp. However, the "light source" is not limited to these.

An amount of ultraviolet ray emitted from the light source varies depending on a component structure of a monomer composition. Normally, the amount is preferably 10 mW/cm$^2$ to 10000 mW/cm$^2$.

A wavelength range of the emitted ultraviolet ray is not particularly limited. The wavelength range is preferably 100 nm to 700 nm, and more preferably 200 nm to 500 nm.

In another embodiment of the present invention, an electron beam may be used as the active energy ray. In a case where the electron beam is used, examples of the "light source" include various electron beam accelerators such as a Cockcroft accelerator, a Cockcroft-Walton accelerator, a Van de Graaff accelerator, a resonance transformer accelerator, an insulated core transformer accelerator, a liner accelerator, a dynamitron accelerator, a high-frequency accelerator, and an electron curtain accelerator. However, the "light source" is not limited to these.

The position control apparatus (position control means) 11 is a device for carrying out position control so that light from the color difference meter (cure state check means) 12 is directed to the part in which the cure degree of the active energy ray-curable resin composition is evaluated. The position control apparatus (position control means) 11 includes an image recognition apparatus (not illustrated) for recognizing the part in which the cure degree of the active energy ray-curable resin composition is evaluated and movement means (not illustrated) for moving the evaluation sample 16 provided on the stage 15 in a horizontal direction so that the light from the color difference meter (cure state check means) 12 is directed to the part in which the cure degree of the active energy ray-curable resin composition is evaluated.

The color difference meter (cure state check means) 12 measures a color value of the part in which the cure degree of the active energy ray-curable resin composition is evaluated. For example, the color difference meter (cure state check means) 12 directs an incident ultraviolet ray from above to a part of the evaluation sample 16 which part is to be evaluated, so as to measure the color value by use of light reflected from the part. The "cure state check means" is not particularly limited provided that the "cure state check means" can measure the color value. For example, a spectrophotometer, a color luminance meter, and the like in addition to the color difference meter are preferably usable as the cure state check means. However, the cure state check means is not limited to these.

The testing software (evaluation means) 13 evaluates the cure degree of the active energy ray-curable resin composition in accordance with the color value measured by use of the color difference meter 12 and transmits a result of the evaluation to the sorting apparatus (sorting means) 14. The "evaluation means" is exemplified by software having a function of determining, by use of the color value, whether or not there is a significant difference between a color of the active energy ray-curable resin composition and a reference color or determining that the color value of the active energy ray-curable resin composition falls within a reference value preliminarily set in accordance with a correlation between a cure degree of a resin composition and a reference color. However, the "evaluation means" is not limited to this.

The sorting apparatus (sorting means) 14 determines whether or not the active energy ray-curable resin composition whose cure degree has been evaluated is acceptable and classifies the active energy ray-curable resin composition as an acceptable product or an unacceptable product. Specifically, the sorting apparatus (sorting means) 14 preferably has a function of sorting acceptable products from unacceptable products. The "sorting means" is not particularly limited provided that the "sorting means" has a function of sorting acceptable products from unacceptable products.

Note that an active energy ray-curable resin composition to be evaluated by use of the cure degree evaluation system in accordance with the present invention also includes a cure degree check sheet in accordance with the present invention. For example, in a case where the cure degree check sheet is used in the cure degree evaluation system, the cure state check means measures a color value of the cure degree check sheet and evaluates a cure degree of the cure degree check sheet in accordance with the color value thus measured. In a case where it is determined from a result of the evaluation of the cure degree check sheet whether or not the cure degree of the cure degree check sheet is acceptable, it is possible to indirectly determine whether or not a cure degree of an active energy ray-curable resin composition is acceptable, the active energy ray-curable resin composition having been irradiated with an active energy ray simultaneously with the cure degree check sheet and containing no leuco dye.

[4. Cure Degree Check Sheet]

A cure degree check sheet in accordance with the present invention is as described earlier in "1-2. Cure Degree Check Sheet".

The cure degree evaluation method in accordance with the present invention for evaluating a cure degree of an active energy ray-curable resin composition is preferably arranged such that the leuco dye is at least one kind selected from the group consisting of leuco crystal violet, leuco malachite green, leuco crystal violet lactone, leuco quinizarine, benzoyl leucomethylene blue, 2'-(2-chloroanilino)-6'-(dibutylamino) fluorane, and 3',6'-bis(dimethylamino)-2-(4-nitrophenyl) spiro[isoindole-1,9'-xanthene]-3-on.

According to the arrangement, it is possible to evaluate the cure degree highly accurately since a color of the active energy ray-curable resin composition greatly changes.

The cure degree evaluation method in accordance with the present invention for evaluating a cure degree of an active energy ray-curable resin composition is preferably arranged such that the radical polymerization compound is at least one kind selected from the group consisting of acrylate, methacrylate, vinyl ether, and allyl ether.

According to the arrangement, it is possible to shorten curing time since the active energy ray-curable resin composition has high curing reactivity.

The cure degree evaluation method in accordance with the present invention for evaluating a cure degree of an active energy ray-curable resin composition is preferably arranged such that the cure degree of the active energy ray-curable resin composition is evaluated by comparing the color of the active energy ray-curable resin composition and a reference color.

In a case where the cure degree is visually evaluated by comparing the color of the active energy ray-curable resin composition and the reference color, it is possible to simply determine whether or not the active energy ray-curable resin composition has a cure degree which is not less than a certain level.

The cure degree evaluation method in accordance with the present invention for evaluating a cure degree of an active energy ray-curable resin composition is preferably arranged such that the cure degree of the active energy ray-curable resin composition is evaluated by measuring a color value of the active energy ray-curable resin composition.

A color value is obtained by quantitatively representing a color. For example, the color value can be measured by use of a color difference meter. In a case where a color value of an active energy ray-curable resin composition is measured and a cure degree of the active energy ray-curable resin composition is found based on a correlation between the obtained color value and a cure state of the active energy ray-curable resin composition, it is possible to grasp not only whether or not the active energy ray-curable resin composition is cured but also to what degree the active energy ray-curable resin composition is cured. Further, since a cure degree of the active energy ray-curable resin composition can be converted into a numerical value merely by measuring a color value of the active energy ray-curable resin composition, it is possible to carry out a product quality evaluation easily.

The cure degree evaluation method in accordance with the present invention for evaluating a cure degree of an active energy ray-curable resin composition is preferably arranged such that a part in which the cure degree of the active energy ray-curable resin composition is evaluated is provided separately from a part to which the active energy ray-curable resin composition is to be applied.

In an actual product, it may be difficult to evaluate a colored degree of an active energy ray-curable resin composition when a part to which the active energy ray-curable resin composition is to be applied is indefinite in shape. In view of the circumstances, for example, in a case where a part which is easy to test is provided by preparing a lead-in part separately from a part to which the active energy ray-curable resin composition is to be applied, that is, by preparing a part to which the active energy ray-curable resin composition is applied separately from the part to which the active energy ray-curable resin composition is to be applied. This makes it possible to carry out a cure degree evaluation easily even with respect to a sample which is indefinite in shape.

The cure degree evaluation method in accordance with the present invention for evaluating a cure degree of an active energy ray-curable resin composition is preferably arranged such that the active energy ray-curable resin composition further contains an inorganic filler.

The active energy ray-curable resin composition further containing the inorganic filler is entirely cloudy. In this case, a change in color of the active energy ray-curable resin composition can be visually checked more easily than in the case of an active energy ray-curable resin composition which is transparent and contains no inorganic filler. This makes it easy to carry out a cure degree evaluation. Furthermore, such an active energy ray-curable resin composition yields an effect of enhancing rigidity of the active energy ray-curable resin composition. Moreover, such an active energy ray-curable resin composition yields an effect of reducing a shrinkage of a cured resin.

The cure degree check sheet in accordance with the present invention is preferably arranged such that the cure degree check sheet is obtained by semi-curing the chemical solution applied to the sheet-formed transparent resin material.

The cure degree evaluation method in accordance with the present invention for evaluating a cure degree of an active energy ray-curable resin composition is preferably arranged such that the cure degree of the active energy ray-curable resin composition is evaluated by comparing the color of the cure degree check sheet and a reference color.

The cure degree evaluation method in accordance with the present invention for evaluating a cure degree of an active energy ray-curable resin composition is preferably arranged such that the cure degree of the active energy ray-curable resin composition is evaluated by measuring a color value of the cure degree check sheet.

According to the arrangement, it is possible to indirectly but simply and promptly evaluate a cure degree of an active energy ray-curable resin composition subjected to active energy ray irradiation while checking a colored degree of the cure degree check sheet. Further, since it is easy to measure a color value of the cure degree check sheet, it is easy to evaluate the cure degree of the active energy ray-curable resin composition. Accordingly, a shape of a part to which an active energy ray-curable resin composition is applied is less likely to restrict an evaluation of a cure degree of the active energy ray-curable resin composition.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following description more specifically discusses the present invention by use of Examples. However, the present invention is not limited to this.

Example 1

<Cure Degree Evaluation by Cure Degree Measurement Method in Accordance with the Present Invention>

[1. Preparation of Cured Product of Active Energy Ray-Curable Resin Composition]

A chemical solution was prepared as an active energy ray-curable resin composition by mixing chemical compounds shown in Table 1 so as to cause the mixed chemical compounds to have 100% by weight in total, and the chemical solution was applied to a glass substrate in a suitable amount. Thereafter, a glass slide was placed on the glass substrate via a thickness gauge of 50 μm, and ultraviolet irradiation was carried out by use of a mercury lamp at 20 mW/cm$^2$ for 60 seconds. Then, a cured product of the active energy ray-curable resin composition of F.T. 50 μm was obtained on the glass slide.

TABLE 1

|  | wt % |
|---|---|
| Polymerization initiator (Lucirin TPO, produced by BASF A.G.) | 1 |
| Silica | 70 |
| Isobornyl acrylate (IBX-A, produced by KYOEISHA CHEMICAL Co., LTD.) | 8.95 |
| Phthalic acid acrylate (HOA-HH, produced by KYOEISHA CHEMICAL Co., LTD.) | 7 |
| Urethane oligomer | 7 |
| Polycarbonate urethane oligomer | 6 |
| Leuco crystal violet | 0.05 |

[2. Cure Degree Evaluation]

(2-1. Visual Check of Cure State)

(Visual Check Method)

Comparative samples for a visual check were prepared by a method similar to that described in "1. Preparation of Cured Product of Active Energy Ray-curable Resin Composition", except that active energy ray irradiation time was set to 5 seconds, 40 seconds, 60 seconds, and 80 seconds.

The cured product (hereinafter referred to as an "object sample") of the active energy ray-curable resin composition obtained in "1. Preparation of Cured Product of Active Energy Ray-curable Resin Composition" and the comparative samples were subjected to visual color depth determination. Table 2 shows a result of the determination. In Table 2, a circle indicates a case where a color of a comparative sample is deeper than that of the object sample and an X indicates a case where a color of a comparative sample is lighter than that of the object sample.

TABLE 2

| UV irradiation time (sec.) | Evaluation |
|---|---|
| 5 | x |
| 40 | x |
| 60 | ○ |
| 80 | ○ |

As a result of the visual check, it was confirmed, even by visual evaluation, that the comparative samples subjected to short-time active energy ray irradiation for 5 seconds and 40 seconds were less colored and were less active energy ray curable than the object sample. Namely, even in a case where a difference in active energy ray irradiation time was 20 seconds or so, it was possible to visually check a difference in cure state of an active energy ray by comparing colored degrees of the active energy ray-curable resin compositions. From this result, it was confirmed that it was possible to accurately sort out unacceptable products produced due to various causes occurring in a production site. Since a malfunction occurs mainly due to an insufficiently cured active energy ray-curable resin composition in an actual production site, a comparison with a color of a sample of a cured acceptable product made it possible to check a cure state of an active energy ray-curable resin composition for each product.

(2-2. Cure State Evaluation by Color Value Measurement)

(Color Value Measurement Method)

For the active energy ray-curable resin compositions obtained in "1. Preparation of Cured Product of Active Energy Ray-curable Resin Composition", color values of X, Y, and Z of an xyz color system were measured by use of a color difference meter (model number: Spectrophotometer CM-3600d, produced by Konica Minolta Sensing, Inc.) in a reflectance measurement mode. Table 3 shows the X, Y, and Z color values of the active energy ray-curable resin compositions for each ultraviolet irradiation time.

TABLE 3

| UV irradiation time (sec.) | X (—) | Y (—) | Z (—) |
|---|---|---|---|
| 0.5 | 8.39 | 6.86 | 20.35 |
| 2 | 7.95 | 6.62 | 18.25 |
| 5 | 7.85 | 6.46 | 17.86 |

TABLE 3-continued

| UV irradiation time (sec.) | X (—) | Y (—) | Z (—) |
|---|---|---|---|
| 10 | 7.73 | 6.33 | 17.53 |
| 30 | 7.44 | 6.16 | 16.17 |
| 60 | 7.33 | 6.07 | 15.71 |
| 150 | 7.17 | 6.14 | 14.79 |

Next, a cure degree evaluation was carried out from the obtained X, Y, and Z color values. As described in "1-3. Cure Degree Evaluation Method" of "Description of Embodiments", assume that each of X, Y, and Z color values obtained 0.5 second after ultraviolet irradiation is a cure degree of 0% and each of X, Y, and Z color values obtained 150 seconds after ultraviolet irradiation is a cure degree of 100%. For example, in a case where the X color value is $X_t$ t seconds after ultraviolet irradiation, an evaluation formula for a cure degree of an active energy ray-curable resin composition subjected to ultraviolet irradiation for t seconds can be represented by the following equation (1). Y and Z cure degrees can be similarly found.

$$\text{Cure degree (\%)} = |(X_t - X_{0.5})/(X_{150} - X_{0.5})| \times 100 \quad (1)$$

Figure 2:
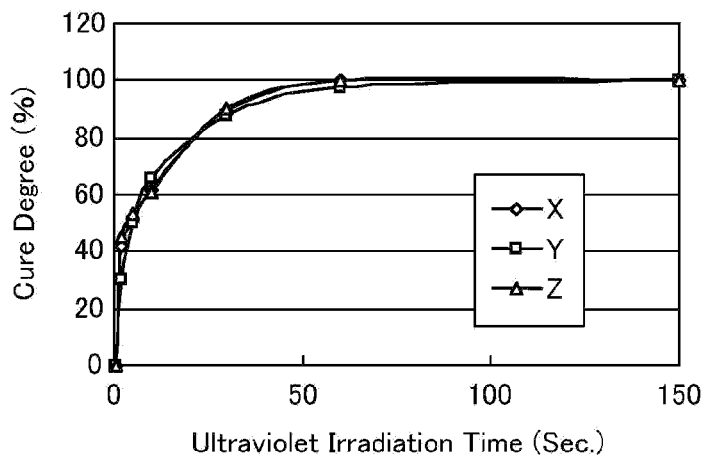
FIG. 2 is a graph showing a relationship between ultraviolet irradiation time and cure degrees calculated from X, Y, and Z color values.

The X, Y, and Z cure degrees for each ultraviolet irradiation time shown in Table 3 were calculated. FIG. 2 shows a result of the calculation. FIG. 2 is a graph showing a relationship between ultraviolet irradiation time and cure degrees calculated from the X, Y, and Z color values.

It was confirmed that each of the cure degrees calculated from the X, Y, and Z color values gradually increased in accordance with a length of ultraviolet irradiation time.

[3. Measurement Accuracy Evaluation]

Next, an evaluation was carried out for measurement accuracy of a method for measuring a cure degree of a cured product of an active energy ray-curable resin composition in accordance with the present invention. A chemical solution was prepared as an active energy ray-curable resin composition by mixing chemical compounds shown in Table 1 so as to cause the mixed chemical compounds to have 100% by weight in total, and the chemical solution was applied to a glass substrate in a suitable amount. Thereafter, a glass slide was placed on the glass substrate via a thickness gauge of 50 μm, and ultraviolet irradiation was carried out at 20 mW/cm². The ultraviolet irradiation was carried out for 10 seconds or 60 seconds, so as to cure the active energy ray-curable resin composition. Then, a sample 1 for a measurement accuracy evaluation was obtained. Samples 2 through 5 for the measurement accuracy evaluation were similarly obtained. X, Y, and Z color values were measured for the obtained samples 1 through 5 of the active energy ray-curable resin composition. Note that standard deviations (3σ) for the samples 1 through 5 were found by tripling standard deviations for the X, Y, and Z color values measured for the samples 1 through 5.

TABLE 4

| | Curing time (10 sec.) | | | Curing time (60 sec.) | | |
|---|---|---|---|---|---|---|
| | X | Y | Z | X | Y | Z |
| Sample 1 | 7.77 | 6.33 | 17.53 | 7.33 | 6.07 | 15.71 |
| Sample 2 | 7.79 | 6.35 | 17.55 | 7.34 | 6.05 | 15.69 |
| Sample 3 | 7.76 | 6.34 | 17.53 | 7.36 | 6.09 | 15.73 |
| Sample 4 | 7.72 | 6.36 | 17.51 | 7.33 | 6.05 | 15.70 |
| Sample 5 | 7.71 | 6.33 | 17.54 | 7.37 | 6.08 | 15.71 |
| Average | 7.75 | 6.34 | 17.53 | 7.35 | 6.07 | 15.71 |
| 3σ | 0.1017 | 0.0391 | 0.0444 | 0.0545 | 0.0541 | 0.0445 |

The 3σ values of the X, Y, and Z color values for the samples 1 through 5 revealed that there was less variation in measurement result obtained by use of a method for measuring a cure degree of the active energy ray-curable resin composition in accordance with the present invention.

Table 5 shows a result of conversion from the X, Y, and Z color values shown in Table 4 to cure degrees by use of the equation (1).

TABLE 5

| | Curing time (10 sec.) | | | Curing time (60 sec.) | | |
|---|---|---|---|---|---|---|
| | X | Y | Z | X | Y | Z |
| Sample 1 | 61.4 | 65.9 | 60.8 | 100.2 | 97.9 | 100.0 |
| Sample 2 | 59.5 | 63.4 | 60.4 | 99.2 | 100.7 | 100.4 |
| Sample 3 | 60.5 | 64.7 | 60.8 | 97.4 | 95.8 | 99.6 |
| Sample 4 | 63.3 | 62.2 | 61.2 | 100.2 | 100.7 | 100.2 |
| Sample 5 | 58.6 | 65.9 | 60.6 | 96.4 | 97.0 | 100.0 |
| Average | 60.7 | 64.4 | 60.8 | 98.7 | 98.4 | 100.0 |
| 3σ | 5.5 | 4.9 | 1.0 | 5.2 | 6.7 | 1.0 |

All the 3σ values indicating accuracy of measurement of the obtained X, Y, and Z cure degrees were much smaller than 3σ values of cure degrees obtained by use of measurement methods of Comparative Example 1 (an FT-IR method) and Comparative Example 2 (a method for finding a Young's modulus) (which are described later) (see Table 5). Accordingly, it was proved that the method for measuring the cure degree of the active energy ray-curable resin composition in accordance with the present invention enabled a cure degree evaluation with higher accuracy than the measurement methods of Comparative Examples 1 and 2. A cure degree of an active energy ray-curable resin composition has not been evaluated, whereas it was confirmed that the method for measuring the cure degree of the active energy ray-curable resin composition in accordance with the present invention had accuracy sufficient for a practical quality evaluation in the step of curing an active energy ray-curable resin composition.

Comparative Example 1

<Cure Degree Evaluation by FT-IR Method>

[1. Preparation of Cured Product of Active Energy Ray-Curable Resin Composition]

A cured product of an active energy ray-curable resin composition was prepared by a method similar to that described in Example 1.

[2. Cure Degree Evaluation]

(FT-IR Method)

For the cured product of the active energy ray-curable resin composition obtained in "1. Preparation of Cured Product of Active Energy Ray-curable Resin Composition", an evaluation of a cure degree of an active energy ray-curable resin composition was carried out by use of the FT-IR method. In the present example, for (i) an active energy ray-curable resin composition which had not been subjected to ultraviolet irradiation and was uncured and (ii) cured products of the active energy ray-curable resin composition which were obtained by curing the active energy ray-curable resin composition with ultraviolet irradiation time changed, areas of an absorbance peak of C=C group (1630 cm$^{-1}$) and an absorbance peak of C=O group (1730 cm$^{-1}$) were measured by use of an FT-IR (model number: system2000, produced by PerkinElmer Co., Ltd.) to which Golden Gate Diamond ATR was attached.

A reaction rate ($A_t$) of a curing reaction of the active energy ray-curable resin composition subjected to ultraviolet irradiation for t seconds was calculated from a peak area for C=C group of a cured product of the active energy ray-curable resin composition subjected to ultraviolet irradiation for t seconds (hereinafter referred to as a C=C peak area obtained t seconds after ultraviolet irradiation), the peak area being normalized by a peak area for C=O group of the cured product of the active energy ray-curable resin composition subjected to ultraviolet irradiation for t seconds (hereinafter referred to as a C=O peak area obtained t seconds after ultraviolet irradiation). Namely, the reaction rate ($A_t$) was found by use of the following equation:

Reaction rate ($A_t$)=C=C peak area obtained $t$ seconds after ultraviolet irradiation/C=O peak area obtained $t$ seconds after ultraviolet irradiation   (2)

Next, a cure degree was evaluated assuming that a reaction rate ($A_{0.5}$) obtained 0.5 second after ultraviolet irradiation was a cure degree of 0% and a reaction rate ($A_{150}$) obtained 150 seconds after ultraviolet irradiation was a cure degree of 100%. Namely, in a case where the FT-IR method is used and the reaction rate obtained t seconds after ultraviolet irradiation is $A_t$, an evaluation formula for a cure degree of the cured product of the active energy ray-curable resin composition subjected to ultraviolet irradiation for t seconds can be represented by the following equation (3):

Cure degree (%)=|{$A_t$−($A_{150}$−$A_{0.5}$)}/($A_{150}$−$A_{0.5}$)|×100   (3)

Figure 3:
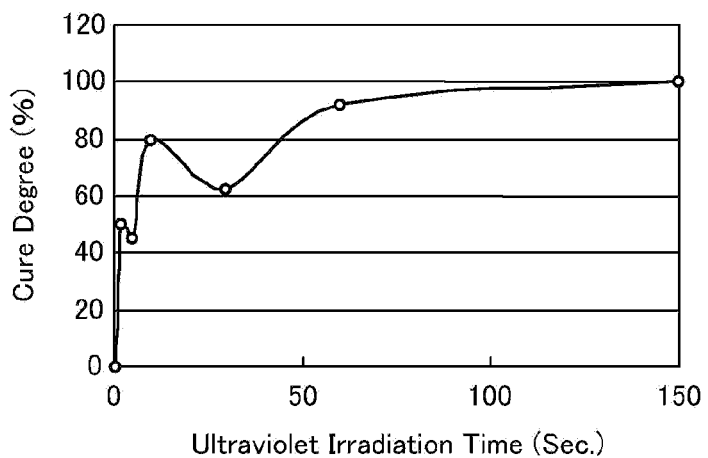
FIG. 3 is a graph showing a relationship between ultraviolet irradiation time and a cure degree measured by use of the FT-IR method.

FIG. 3 shows a result of a cure degree obtained by use of the equation (3). FIG. 3 is a graph showing a relationship between ultraviolet irradiation time and a cure degree measured by use of the FT-IR method.

Macroscopically, the cure degree tends to increase in accordance with ultraviolet irradiation time. However, locally, the cure degree has downward-sloping parts in the graph as shown from 2 seconds to 5 seconds after ultraviolet irradiation and from 10 seconds to 30 seconds after ultraviolet irradiation. Therefore, it was revealed that the cure degree was not evaluated accurately as a whole.

[3. Measurement Accuracy Evaluation]

Next, evaluation accuracy was checked as in the case of Example 1. Samples 1 through 5 for a measurement accuracy evaluation which were subjected to ultraviolet irradiation for 10 seconds or 60 seconds were prepared. Then, a cure degree evaluation was carried out by use of the equation (3). The values $A_{150}$ and $A_0$ obtained in [2. Cure Degree Evaluation] were used to calculate a cure degree. Table 6 shows cure degrees of the samples 1 through 5.

TABLE 6

|  | Curing time (10 sec.) | Curing time (60 sec.) |
| --- | --- | --- |
| Sample 1 | 79.4 | 91.9 |
| Sample 2 | 60.2 | 84.5 |
| Sample 3 | 60.3 | 92.0 |
| Sample 4 | 50.8 | 70.2 |
| Sample 5 | 74.2 | 83.9 |
| Average | 66.0 | 84.5 |
| 3σ | 34.0 | 26.7 |

This revealed that a cure degree measured by use of the FT-IR method was evaluated with extremely low accuracy and it was difficult to stably carry out quality control. This is because a measurement error is large since in order to measure C=C and C=O peak areas, the C=C and C=O peak areas need to be calculated from a broad absorbance peak. Further, a measurement sensitivity of the FT-IR method seems to be insufficient to evaluate a cure degree. In view of these points, the cure degree evaluation by use of the FT-IR method is considered to be much inferior to the cure degree evaluation method in accordance with the present invention for evaluating a cure degree of an active energy ray-curable resin composition.

Comparative Example 2

<Cure Degree Evaluation by Young's Modulus Measurement>

As a common method for evaluating a cure degree of an active energy ray-curable resin composition, a cure degree of a cured product was evaluated by a magnitude of a Young's modulus as in the case of the FT-IR method carried out in Comparative Example 1.

[1. Preparation of Cured Product of Active Energy Ray-Curable Resin Composition]

A cured product of an active energy ray-curable resin composition was prepared by a method similar to that described in Example 1.

[2. Cure Degree Evaluation]

(Young's Modulus Measurement Method)

A Young's Modulus of the cured product of the active energy ray-curable resin composition obtained in "1. Preparation of Cured Product of Active Energy Ray-Curable Resin Composition" was measured. The Young's Modulus can be measured by use of a conventionally publicly-known method (see the description of "New Technology of UV/EB Curing and Application, p. 55, CMC Publishing CO., LTD.). In the present example, the Young's Modulus of the cured product of the active energy ray-curable resin composition was measured by use of a Fischer hardness tester (model number: WIN-HCU, produced by Fischer Instruments K.K.) by causing a Vickers indenter to carry out needling and drawing in a load increment mode at a speed of 1 mN/s.

A cure degree was calculated assuming that a Young's Modulus ($E_{0.5}$) of the cured product of the active energy ray-curable resin composition subjected to ultraviolet irradiation for 0.5 second was a cure degree of 0% and a Young's Modulus ($E_{150}$) of the cured product of the active energy ray-curable resin composition subjected to ultraviolet irradiation for 150 seconds was a cure degree of 100%. In a case where the Young's Modulus of the cured product of the active energy ray-curable resin composition subjected to ultraviolet irradiation for t seconds is $E_t$, a cure degree of the cured product of the active energy ray-curable resin composition subjected to ultraviolet irradiation for t seconds can be represented by the following equation (4).

Cure degree (%)=($E_t$−$E_{0.5}$)/($E_{150}$−$E_{0.5}$)×100   (4)

Figure 4:
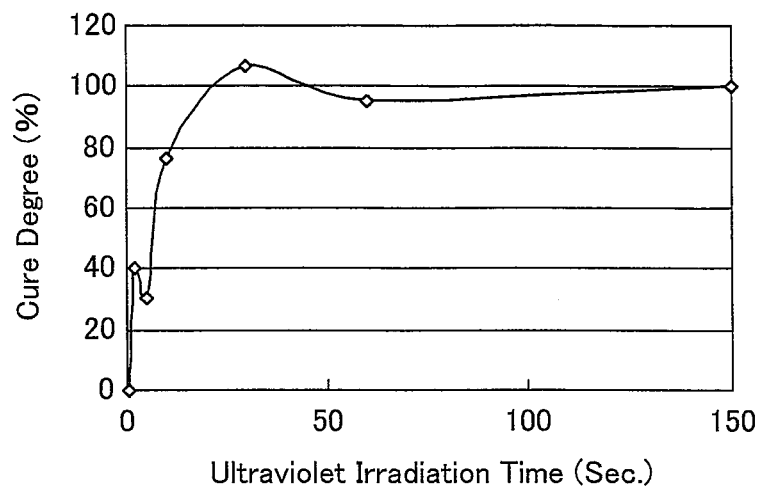
FIG. 4 is a graph showing a cure degree of a cured product of an active energy ray-curable resin composition for each ultraviolet irradiation time.

FIG. 4 shows a result of calculation by use of the equation (4). FIG. 4 is a graph showing a cure degree of a cured product of an active energy ray-curable resin composition for each ultraviolet irradiation time.

An obtained result is locally inconsistent though the cure degree changes in accordance with ultraviolet irradiation time (see FIG. 4). This is due to a measurement error in the hardness tester and difficult to improve. The Young's modulus measurement method is also considered to be much inferior in evaluation accuracy to the cure degree evaluation method in accordance with the present invention for evaluating a cure degree of an active energy ray-curable resin composition.

[3. Measurement Accuracy Evaluation]

Next, evaluation accuracy was checked as in the case of Example 1. Samples 1 through 5 for a measurement accuracy evaluation which were subjected to ultraviolet irradiation for 10 seconds or 60 seconds were prepared. Then, a cure degree evaluation was carried out by use of the equation (4). The values $A_{150}$ and $A_0$ obtained in [2. Cure Degree Evaluation] were used to calculate a cure degree. Table 7 shows cure degrees of the samples 1 through 5.

TABLE 7

|  | Curing time (10 sec.) | Curing time (60 sec.) |
|---|---|---|
| Sample 1 | 76.7 | 95.4 |
| Sample 2 | 62.0 | 88.6 |
| Sample 3 | 87.6 | 103.8 |
| Sample 4 | 58.3 | 88.2 |
| Sample 5 | 73.1 | 72.5 |
| Average | 71.5 | 89.7 |
| 3σ | 35.3 | 34.5 |

From this result, it was confirmed that the cure degree evaluation by use of a Young's Modulus has insufficient accuracy and is much inferior in accuracy to the method for measuring the cure degree of the active energy ray-curable resin composition in accordance with the present invention.

Example 2

An active energy ray-curable resin composition was prepared by a method similar to that described in Example 1, except that leuco malachite green was used as a leuco dye and ultraviolet irradiation time was optional. Table 8 shows a composition of the chemical solution thus prepared. FIG. 8 shows a colored degree of the active energy ray-curable resin composition of Example 2 for each ultraviolet irradiation time.

Example 3

An active energy ray-curable resin composition was prepared by a method similar to that described in Example 1, except that leuco crystal violet lactone was used as a leuco dye and ultraviolet irradiation time was optional. Table 8 shows a composition of the chemical solution thus prepared. FIG. 8 shows a colored degree of the active energy ray-curable resin composition of Example 3 for each ultraviolet irradiation time.

Example 4

An active energy ray-curable resin composition was prepared by a method similar to that described in Example 1, except that leuco quinizarine was used as a leuco dye and ultraviolet irradiation time was optional. Table 8 shows a composition of the chemical solution thus prepared. FIG. 8 shows a colored degree of the active energy ray-curable resin composition of Example 4 for each ultraviolet irradiation time.

Example 5

An active energy ray-curable resin composition was prepared by a method similar to that described in Example 1, except that benzoyl leucomethylene blue was used as a leuco dye and ultraviolet irradiation time was optional. Table 8 shows a composition of the chemical solution thus prepared. FIG. 8 shows a colored degree of the active energy ray-curable resin composition of Example 5 for each ultraviolet irradiation time.

Example 6

An active energy ray-curable resin composition was prepared by a method similar to that described in Example 1, except that 2'-(2-chloroanilino)-6'-(dibutylamino)fluorane was used as a leuco dye and ultraviolet irradiation time was optional. Table 8 shows a composition of the chemical solution thus prepared. FIG. 8 shows a colored degree of the active energy ray-curable resin composition of Example 6 for each ultraviolet irradiation time.

Example 7

An active energy ray-curable resin composition was prepared by a method similar to that described in Example 1, except that 3',6'-bis(dimethylamino)-2-(4-nitrophenyl)spiro[isoindole-1,9'-xanthene]-3-on was used as a leuco dye and ultraviolet irradiation time was optional. Table 8 shows a composition of the chemical solution thus prepared. FIG. 8 shows a colored degree of the active energy ray-curable resin composition of Example 7 for each ultraviolet irradiation time. Note that each of 0.5 s to 150 s shown in FIG. 8 indicates ultraviolet irradiation time (second(s)).

TABLE 8

|  | Ex. 2 | Ex. 3 | Ex. 4 | Ex. 5 | Ex. 6 | Ex. 7 |
|---|---|---|---|---|---|---|
| Polymerization initiator (Lucirin TPO, produced by BASF A.G.) | 1 | 1 | 1 | 1 | 1 | 1 |
| Silica | 70 | 70 | 70 | 70 | 70 | 70 |
| Isobornyl acrylate (IBX-A, produced by KYOEISHA CHEMICAL Co., LTD.) | 8.95 | 8.95 | 8.95 | 8.95 | 8.95 | 8.95 |
| Phthalic acid acrylate (HOA-HH, produced by KYOEISHA CHEMICAL Co., LTD.) | 7 | 7 | 7 | 7 | 7 | 7 |
| Urethane oligomer | 7 | 7 | 7 | 7 | 7 | 7 |
| Polycarbonate urethane oligomer | 6 | 6 | 6 | 6 | 6 | 6 |
| Leuco malachite green (produced by Kishi Kasei Co., Ltd.) | 0.05 |  |  |  |  |  |
| Leuco crystal violet lactone (produced by Tokyo Chemical Industry Co., Ltd.) |  | 0.05 |  |  |  |  |
| Leuco quinizarine (produced by Tokyo Chemical Industry Co., Ltd.) |  |  | 0.05 |  |  |  |

TABLE 8-continued

|  | Ex. 2 | Ex. 3 | Ex. 4 | Ex. 5 | Ex. 6 | Ex. 7 |
|---|---|---|---|---|---|---|
| Benzoyl leucomethylene blue (produced by Tokyo Chemical Industry Co., Ltd.) |  |  | 0.05 |  |  |  |
| 2'-(2-chloroanilino)-6'-(dibutylamino)fluorane (produced by Tokyo Chemical Industry Co., Ltd.) |  |  |  | 0.05 |  |  |
| 3',6'-bis(dimethylamino)-2-(4-nitrophenyl)spiro[isoindole-1,9'-xanthene]-3-on |  |  |  |  | 0.05 |  |

It was confirmed that use of any of the leuco dyes in the Examples 2 through 7 caused a change in color in accordance with ultraviolet irradiation time (see FIG. 8). According to this, in a case where it is unfavorable that a product be colored in a specific color, a leuco dye having another color instead of the specific color is usable for the product. Further, a color change is adjustable in accordance with a density of a leuco dye.

Example 8

<Use of Resin Composition Cure Degree Check Sheet>
[1. Preparation of Cure Degree Check Sheet]
A chemical solution was prepared as a resin for preparation of a cure degree check sheet by mixing chemical compounds shown in Table 9 so as to cause the mixed chemical compounds to have 100% by weight in total.

TABLE 9

|  | wt % |
|---|---|
| Polymerization initiator (Lucirin TPO, produced by BASF A.G.) | 0.3 |
| Ethanol | 70 |
| Isobornyl acrylate (IBX-A, produced by KYOEISHA CHEMICAL Co., LTD.) | 9 |
| Phthalic acid acrylate (HOA-HH, produced by KYOEISHA CHEMICAL Co., LTD.) | 6 |
| Urethane polymer | 14.68 |
| Leuco crystal violet | 0.02 |

The resin was screen-printed on a PET sheet having a thickness of 125 μm (model number: Tetoron Film SL type, produced by Teijin DuPont Films Japan Limited) so as to have a thickness of 50 μm. Thereafter, the resin thus screen-printed was baked at 60° C., so that a sheet-formed cure degree check sheet was obtained. Then, the sheet-formed cure degree check sheet was cut out to be handy in size (3 cm×3 cm).

Figure 5:
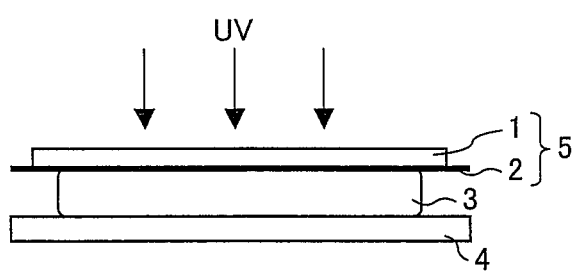
FIG. 5 schematically illustrates a method for evaluating a cure degree of an active energy ray by use of a cure degree check sheet in accordance with the present invention.

[Cure Degree Evaluation]
FIG. 5 schematically illustrates a method for evaluating a cure degree of an active energy ray by use of a cure degree check sheet. FIG. 5 illustrates how the cure degree check sheet is arranged in carrying out ultraviolet irradiation with respect to an active energy ray-curable resin composition.

A cure degree check sheet 5 obtained by screen-printing, on a PET sheet 2, a chemical solution 1 prepared by mixing the chemical compounds shown in Table 9 so as to cause the mixed chemical compounds to have 100% by weight in total and baking the chemical solution 1 thus screen-printed at 60° C. was placed on an active energy ray-curable resin composition 3 dropped on a glass slide 4, so as to be subjected to ultraviolet irradiation (see FIG. 5). Thereafter, the cure degree check sheet 5 which had changed color due to ultraviolet irradiation was taken out, so that a color value of the cure degree check sheet 5 was measured by use of the color difference meter (model number: Spectrophotometer CM-3600d, produced by Konica Minolta Sensing, Inc.).

In a case where a relationship among an ultraviolet irradiation amount, a color value of a cure degree check sheet, and a cure degree of a cured product of an active energy ray-curable resin composition is grasped, the cure degree of the cured product of the active energy ray-curable resin composition can be grasped. According to this method, it is unnecessary to test a product directly. Therefore, the method serves as an extremely advantageous test method in terms of handling during testing and throughput. Further, the method is suitable for a product having a part to which an active energy ray-curable resin composition is applied and which is not desired to be colored.

It was feared that a change in color of the cure degree check sheet placed on the active energy ray-curable resin composition might cause a reduction in ultraviolet transmittance. However, the cure degree check sheet which had been subjected to ultraviolet irradiation at 20 mW/cm$^2$ for 150 seconds was similar in color change to the active energy ray-curable resin composition of Example 1. This cure degree check sheet transmitted an ultraviolet ray having a wavelength of 365 nm at a transmittance of 98.3%. From this result, there seems to be less fear that use of the cure degree check sheet in accordance with the present invention may inhibit curing of an active energy ray-curable resin composition.

INDUSTRIAL APPLICABILITY

According to the present invention, it is possible to evaluate a cure degree of an active energy ray-curable resin composition simply, highly accurately, and quantitatively. Therefore, the present invention is extensively usable for carrying out a product quality evaluation in, for example, various electronics industries using an active energy ray-curable resin composition.

| Reference Signs List | |
|---|---|
| 1 | Chemical solution |
| 2 | PET sheet |
| 3 | Active energy ray-curable resin composition |
| 5 | Cure degree check sheet |
| 10 | Light source (Irradiation means) |
| 11 | Position control apparatus (Position control means) |
| 12 | Color difference meter (Cure state check means) |
| 13 | Testing software (Evaluation means) |
| 14 | Sorting apparatus (Sorting means) |
| 21 | Lead-in section |
| 22 | Part to which active energy ray-curable resin composition is to be applied |
| 23 | Observation window |
| 100 | Cure degree evaluation system |

The invention claimed is:
1. A method for evaluating a cure degree of an active energy ray-curable resin composition, the method comprising the steps of:
    irradiating the active energy ray-curable resin composition with an active energy ray; and
    evaluating the cure degree of the active energy ray-curable resin composition in accordance with a color and a color value of the active energy ray-curable resin composition, the active energy ray-curable resin composition containing at least a radical polymerization compound, a leuco dye, and a radical polymerization initiator; and wherein a part in which the cure degree of the active energy ray-curable resin composition is evaluated is provided separately from a part to which the active energy ray-curable resin composition is being cured, and wherein, in the step of irradiating, the part in which the cure degree of the active energy ray-curable resin composition is evaluated and the part to which the active energy ray-curable resin composition is being cured are simultaneously irradiated with the active energy ray.

2. The method as set forth in claim 1, wherein the leuco dye is at least one kind selected from the group consisting of leuco crystal violet, leuco malachite green, leuco crystal violet lactone, leuco quinizarine, benzoyl leucomethylene blue, 2'-(2-chloroanilino)-6'-(dibutylamino)fluorane, and 3',6'-bis(dimethylamino)-2-(4-nitrophenyl)spiro [isoindole-1,9'-xanthene]-3-on.

3. The method as set forth in claim 1, wherein the radical polymerization compound is at least one kind selected from the group consisting of acrylate, methacrylate, vinyl ether, and allyl ether.

4. The method as set forth in claim 1, wherein the cure degree of the active energy ray-curable resin composition is evaluated by measuring the color of the active energy ray-curable resin composition and comparing the color with a reference color.

5. The method as set forth in claim 1, wherein the active energy ray-curable resin composition further contains an inorganic filler.

6. A cure degree evaluation system for evaluating a cure degree of an active energy ray-curable resin composition containing at least a radical polymerization compound, a leuco dye, and a radical polymerization initiator, the cure degree evaluation system comprising:

a light source for irradiating the active energy ray-curable resin composition with an active energy ray; and one selected from the group consisting of a color difference meter, a spectrophotometer, and a color luminance meter for evaluating the cure degree of the active energy ray-curable resin composition by measuring a color and a color value of a part in which the cure degree of the active energy ray-curable resin composition is evaluated;

wherein a part in which the cure degree of the active energy ray-curable resin composition is evaluated is provided separately from a part to which the active energy ray-curable resin composition is being cured; and wherein the light source simultaneously irradiates, with the active energy ray, the part in which the cure degree of the energy ray-curable resin composition is evaluated and the part to which the active energy rag-curable resin composition is being cured.

7. A method for evaluating a cure degree of an active energy ray-curable resin composition, the method comprising the steps of:

carrying out active energy ray irradiation with respect to a cure degree check sheet simultaneously with active energy ray irradiation with respect to a part to which the active energy ray-curable resin composition is applied; and evaluating the cure degree of the active energy ray-curable resin composition in accordance with a color of the cure degree check sheet, wherein the cure degree check sheet comprises a sheet-formed transparent resin material to which a chemical solution containing at least a radical polymerization compound, a leuco dye, and a radical polymerization initiator is applied, wherein the cure degree of the active energy ray-curable resin composition is evaluated by measuring a color value of the active energy ray-curable resin composition; and wherein a part in which the cure degree of the active energy ray-curable resin composition is evaluated is provided separately from a part to which the active energy ray-curable resin composition is to be applied.

8. The method as set forth in claim 7, wherein the cure degree of the active energy ray-curable resin composition is evaluated by comparing the color of the cure degree check sheet and a reference color.

9. The method as set forth in claim 7, wherein the cure degree of the active energy ray-curable resin composition is evaluated by measuring a color value of the cure degree check sheet.

* * * * *